(12) United States Patent
Martin et al.

(10) Patent No.: US 11,103,226 B2
(45) Date of Patent: Aug. 31, 2021

(54) RETRACTOR SYSTEM WITH TETHERED SURGICAL RETRACTOR

(71) Applicant: Thompson Surgical Instruments, Inc., Traverse City, MI (US)

(72) Inventors: Christopher T. Martin, Empire, MI (US); Adam Truckey, Suttons Bay, MI (US); Dan Farley, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 31 days.

(21) Appl. No.: 16/223,477

(22) Filed: Dec. 18, 2018

(65) Prior Publication Data

US 2019/0183474 A1 Jun. 20, 2019

Related U.S. Application Data

(60) Provisional application No. 62/607,563, filed on Dec. 19, 2017.

(51) Int. Cl.
*A61B 90/57* (2016.01)
*A61B 17/02* (2006.01)
*A61B 17/00* (2006.01)

(52) U.S. Cl.
CPC .............. *A61B 17/02* (2013.01); *A61B 90/57* (2016.02); *A61B 2017/00477* (2013.01); *A61B 2017/0287* (2013.01)

(58) Field of Classification Search
CPC ... A61B 90/57; A61B 2090/571; F16L 3/1058
See application file for complete search history.

(56) References Cited

U.S. PATENT DOCUMENTS

| | | | |
|---|---|---|---|
| RE32,021 E | 11/1985 | Scott, Jr. | |
| 6,368,320 B1* | 4/2002 | Le Couedic | ....... A61B 17/7049 606/250 |
| 6,932,765 B2 | 8/2005 | Berg | |
| 7,309,312 B2* | 12/2007 | Bjork | ..................... A61B 17/02 600/231 |
| 2005/0033118 A1* | 2/2005 | Berg | .................. A61B 17/0293 600/231 |

(Continued)

*Primary Examiner* — Tessa M Matthews
(74) *Attorney, Agent, or Firm* — McAndrews, Held & Malloy, Ltd.

(57) ABSTRACT

A retractor system for securing surgical retractors includes an elastic tether and a cleat. The elastic tether has an elongated side and a predetermined diameter. The cleat includes a base, a head, and a shaft. The base includes an upper surface with a first row of teeth. The head is coupled to the base via the shaft. The head includes a lower surface with a second row of teeth. The first row of teeth are opposite the second row of teeth by less than the predetermined diameter of the tether and are configured to receive and compress the elongated side of the tether. Each tooth of the first row of teeth includes a first gripping surface that extends away from the shaft. Each tooth of the second row of teeth includes a second gripping surface that extends away from the shaft and that is parallel to the first gripping surface of a directly opposite tooth of the first row of teeth.

19 Claims, 7 Drawing Sheets

(56) References Cited

U.S. PATENT DOCUMENTS

| | | | |
|---|---|---|---|
| 2012/0004688 A1* | 1/2012 | Marino | A61B 17/7049 606/251 |
| 2012/0035415 A1* | 2/2012 | Doyle | A61B 90/57 600/102 |
| 2013/0158600 A1* | 6/2013 | Conklin | A61B 17/0483 606/232 |
| 2013/0282028 A1* | 10/2013 | Conklin | A61B 17/0487 606/144 |
| 2018/0051828 A1* | 2/2018 | Boriack | F16L 3/13 |
| 2019/0110786 A1* | 4/2019 | Ip | A61B 17/0218 |
| 2019/0321121 A1* | 10/2019 | Frye | A61B 50/15 |

* cited by examiner

SECTION A-A

RETRACTOR SYSTEM WITH TETHERED SURGICAL RETRACTOR

BACKGROUND

The present disclosure relates to retractor systems and retractors that are used to retract soft tissue and other anatomy of a patient.

During a surgical procedure, a surgeon may make an incision in a patient to access internal organs, bones, and/or other anatomical structures. Retractors may be used to hold back soft tissue and other patient anatomy in the immediate area of the incision. Such retractors may provide the surgeon with an unobstructed view of the internal organs, bones, and/or other anatomical structures. Furthermore, the retractors may maintain an opening via which the surgeon may access the anatomical structures with one or more surgical tools.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure related a retaining system that includes retractors used to retract anatomy in order to provide exposure of an operative site. For example and without limitation, various aspects of the disclosure are directed to a frame having one or more cleats to which retractors may be secured via tethers. The tethers may hold or secure the retractors to the frame in a manner that permits the retractors to react or move in regard to movement of the patient's anatomy. By permitting movement of the retractors, the tethers may help reduce bruising and/or other damage to the patient's anatomy that may result from more stationary retractors that lack such freedom of movement.

DETAILED DESCRIPTION

Figure 1:
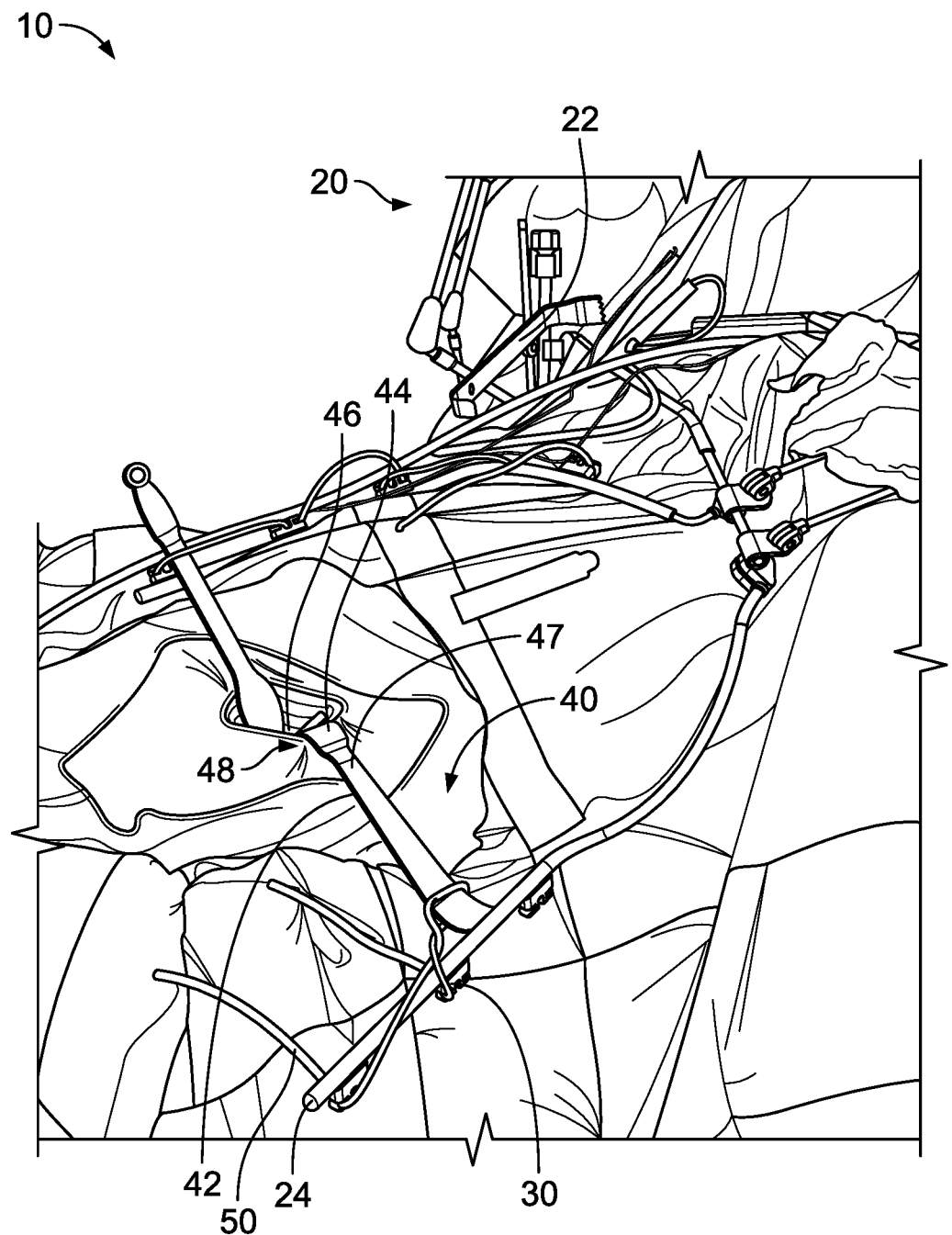
FIG. 1 provides a perspective view of one embodiment of a retractor system used to retract soft tissue of a surgical site in accordance with various aspects of the present disclosure.
Figure 2:
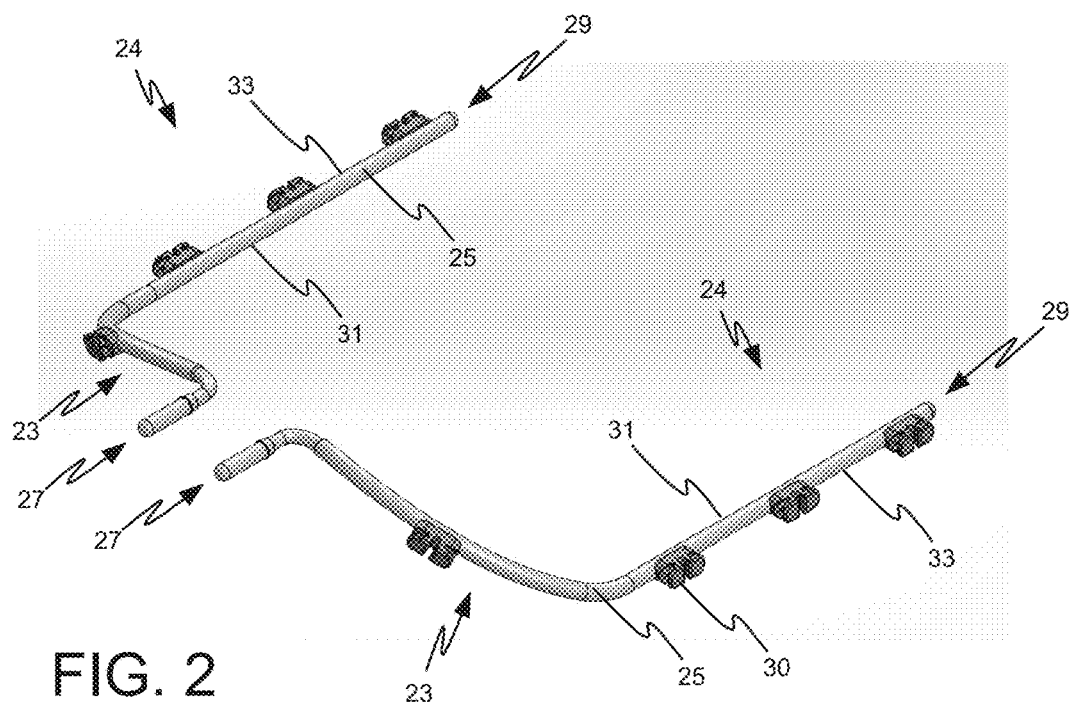
FIGS. 2-6 provide various views of one embodiment of mirrored, frame arms of the retractor system shown in FIG. 1.
Figure 3:
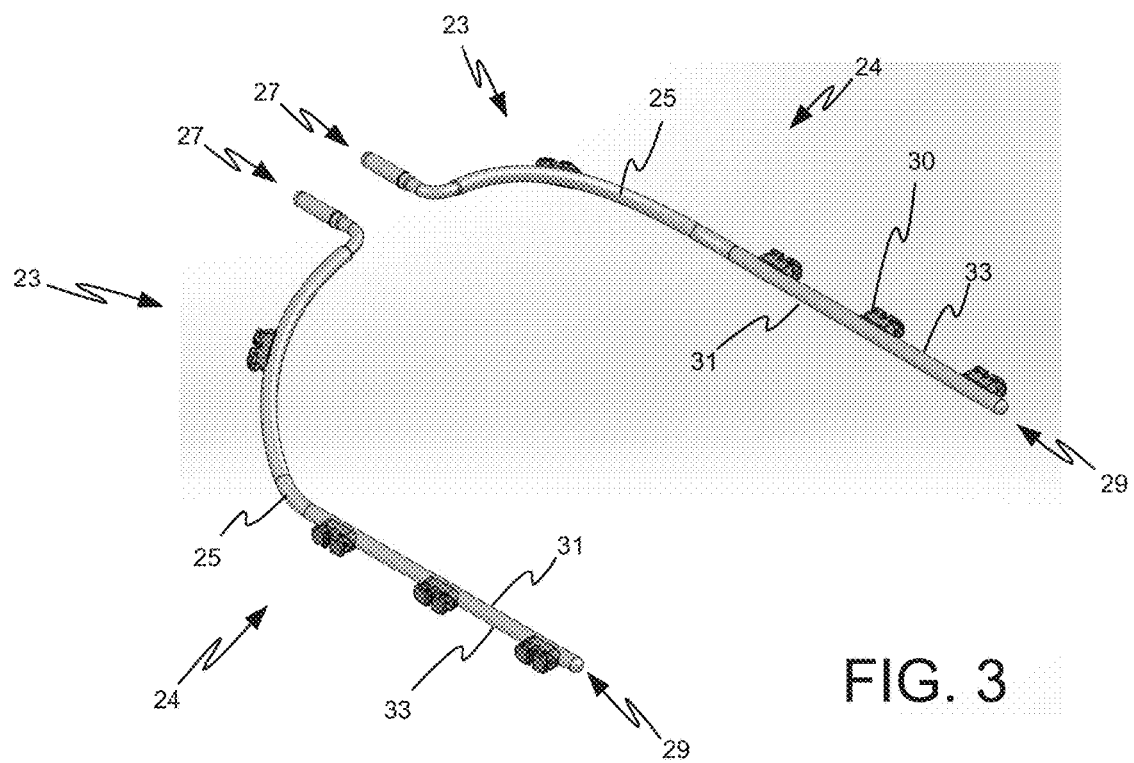

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component, or a first section discussed below could be termed a second element, a second component, or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a device may be turned sideways so that its "top" surface is facing horizontally and its "side" surface is facing vertically, without departing from the teachings of the present disclosure.

In the drawings, various dimensions (e.g., layer thickness, width, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

FIG. 1 illustrates an embodiment of a retractor system 10 in accordance with various aspects of the present disclosure. The retractor system 10 may include a frame assembly 20, a plurality of cleats 30, and a plurality of retractors 40 secured to the plurality of cleats 30 via a plurality of tethers 50.

The frame assembly 20 may include one or more posts 22 and frame arms 24. Each post 22 may be fixed to a rail and/or a hospital bed (not shown) such that the post 22 extends upward in a generally vertical direction. Each post 22 may provide a location to which one or more frame arms 24 may be secured. In the illustrated embodiment, the frame arms 24 generally extend from the posts 22 and toward the center of the hospital bed. Moreover, the frame arms 24 are attached to post 22 and positioned such that the frame arms 24 generally circumscribe a surgical site and distribute a plurality of cleats 30 about a perimeter of the surgical site.

In general, each retractor 40 may include a retractor handle 42 and one or more blades 44 extending from the retractor handle 42. Each blade 44 may comprise a smooth, thin plate with dull edges that is inserted into an incision to pull back the tissue. The blades 44 may come in many different sizes depending on the particular application and physical characteristics of the patient. The blades 44 may be slightly curved or completely flat, and may have end prongs of various configurations to make it easier to pull back tissue.

The a blade 44 may comprise a distal end 46, a proximal end 47, a retracting portion 48. The distal end 46 generally corresponds to the end of the blade 44 inserted into an incision of a patient during a surgical procedure, and the proximal end 47 generally corresponds to the end of the blade 44 extending from the incision and out of the patient during a surgical procedure.

The proximal end 47 adjoins the retractor handle 42, resulting in the retracting portion 48 generally extending or projecting from the retractor handle 42 toward the distal end 46. The retracting portion 48 may be angled with the retractor handle 42. The retracting portion 48 may be sized and adapted to hold back tissue from a site of interest during a procedure. In certain embodiments, the retractor system 10 may include various retractors 40 having a number of differently sized and/or shaped blades 44 to provide increased adaptability for different procedures and/or patients.

As noted above, the retractor handle 42 may be attached to one or more blades 44. As shown, the retractor handle 42 may provide a generally planar upper surface, which may be grasped by the surgeon in order to position the blade 44 appropriately within the incision. Moreover, as explained in more detail below, a tether 50 may by wrapped around the retractor handle 42 to secure the retractors 40 to a cleat 30 of a frame arm 24.

FIGS. 2-6 show various different views of two frame arms 24 to which cleats 30 have been affixed. As shown, each frame arm 24 may comprise a tubular or solid member 25 that extends from a proximal end to a distal end. In some embodiments, the member 26 may have a circular-cross section. See, e.g., the proximal portion 27 shown in FIG. 5. However, in other embodiments, the member 25 may be implemented with other cross-sections such as oval, square, rectangular, hexagonal, or some other shape.

As shown in FIGS. 2-6, each member 25 may be curved such that the each member 25 comprises a curved base portion 23 that adjoins a straight proximal portion 27 to a straight distal portion 29. As shown, one member 25 may be curved in a mirror image of the other member 25 such that base portions 23 and distal portions 29 of the two members 25 generally form a U-shape that projects from the proximal portions 27. To this end, each members 25 may include an inner surface 31 that faces or opposes an inner surface 31 of a paired member 25. As such, the inner, opposing surfaces 31 of paired members 25 may partially circumscribe a region of interest (e.g., a surgical site). Moreover, each member 25 may further include outer surfaces 33 that define an outer edge of the members 25 and that face away from the region partially circumscribed by the inner surfaces 31.

Figure 4:
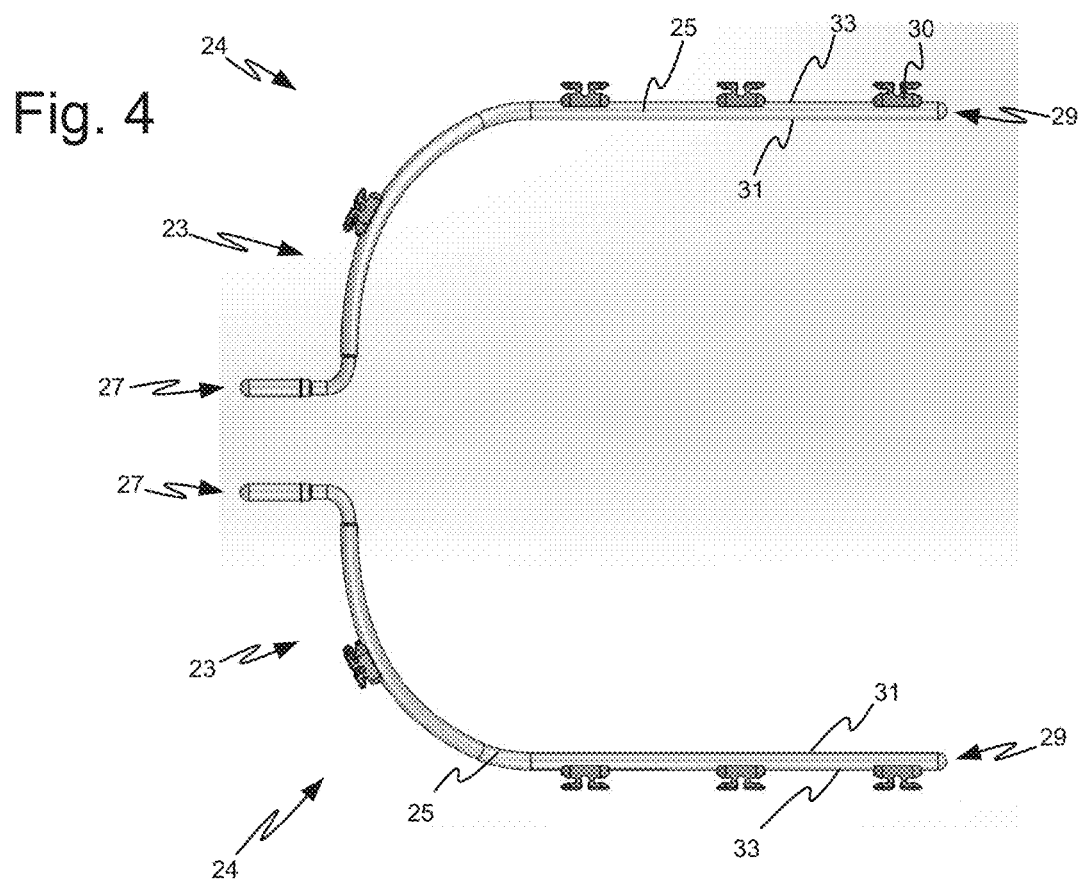

As further shown, each distal portion 29 may extend generally parallel to its respective proximal portion 27. Thus, if the proximal portions 27 of the two frame arms 24 are mounted to the frame assembly 20 such that the proximal portions 27 are generally parallel to each other, then the distal portions 29 may run generally parallel to each other as shown in FIG. 4.

Figure 5:
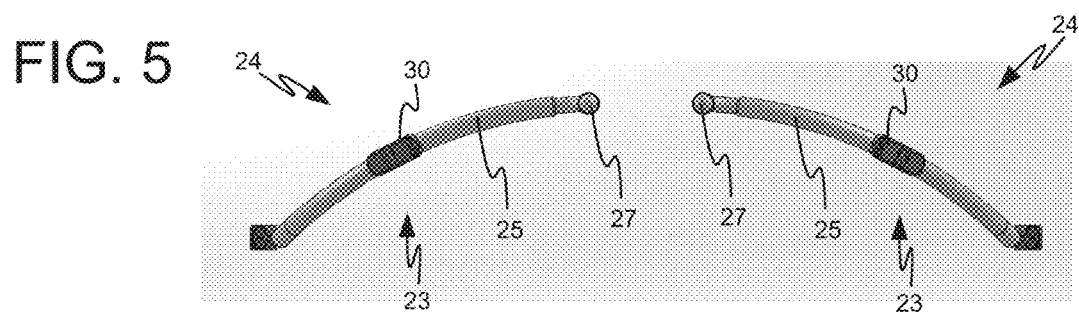
Figure 6:
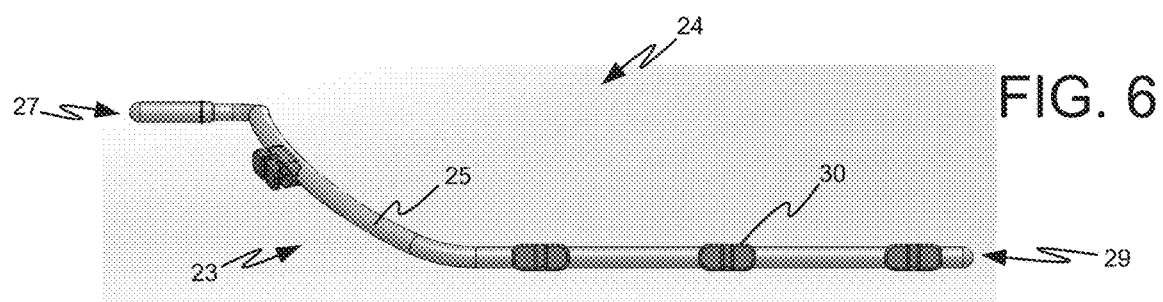

FIGS. 5 and 6 further depict that the proximal portions 27 need not lie in the same plane as their respective distal portions 29. In particular, FIGS. 5 and 6 illustrate an embodiment in which the base portion 23 couples the proximal portion 27 to its respective distal portion 29 such that the proximal portion 27 and its distal portion 29 extend along different, parallel planes. In other embodiments, the base portion 23, proximal portion 27, and distal portion 29 may extend along a single plane. In yet other embodiments, the base portion 23, proximal portion 27, and distal portion 29 may extend along different planes that intersect. In yet other embodiments, the base portion 23, proximal portion 27, and/or distal portion 29 may be curved or otherwise shaped such that the respective portion 23, 27, 29 does not include linear section that extends along a single plane.

FIGS. 2-6 depict an embodiment in which the frame arms 24 are mirror images of one another. However, in other embodiments, the frame arms 24 may be bent differently with respect to each other and/or the frame arms 24 may be of different lengths without departing from certain aspects of the appended claims. Moreover, in some embodiments, the frame assembly 20 may include a single frame arm 24 or more than two frame arms 24.

As further shown in FIGS. 2-6, the frame arms 24 may include one or more cleats 30. In particular, each cleat 30 may be affixed along the outer surface 33 of member 25. More specifically, each cleat 30 may be affixed to the outer surface 33 of the base portion 23, proximal portion 27, and/or the distal portion 29 of the member 25. In general, each cleat 30 may provide an anchor point to which retractors 40 may be anchored or otherwise secured to the frame assembly 20 via a tether 50.

Referring now to FIGS. 7-10 further details regarding one embodiment of a cleat 200. In some embodiments, each cleat 30 of FIGS. 2-6 may be implemented using the cleat 200 of FIGS. 7-10. As shown, the cleat 200 may include a base 210, a shaft 230, and a head 250. The base 210 may generally have a rectangular cuboid or rectangular box shape with tapered or rounded edges. In particular, the base 210 may include an upper surface 212 and a corresponding lower surface 213 that is opposite the upper surface 212, a front surface 214 and a corresponding back surface 215 opposite the front surface 214, and a left surface 216 and a corresponding right surface 217 opposite the left surface 216. In one embodiment, despite the surfaces including various recesses, ridges, and/or tapers, each surface 212, 214, and 216 is generally parallel to its respective corresponding surface 213, 215, 217. Furthermore, in one embodiment, the distance or longitudinal length $L_B$ of the base 210 between the left surface 216 and the right surface 217 is greater than the lateral distance or width $W_B$ of the base 210 between the front surface 214 and the back surface 215. Furthermore, the width $W_B$ of the base 210 in the depicted embodiment is greater than the vertical distance or height $H_B$ between the upper surface 212 and the lower surface 213. However, other embodiments of the base 210 may possess a different distal relationship between the surfaces 212-217.

Similarly, the head 250 may generally have a rectangular cuboid or rectangular box shape with tapered or rounded edges. In particular, the head 250 may include a lower surface 252 and a corresponding upper surface 253 that is opposite the lower surface 252, a front surface 254 and a corresponding back surface 255 opposite the front surface 254, and a left surface 256 and a corresponding right surface 257 opposite the left surface 256. In one embodiment, despite the surfaces including various recesses, ridges, and/ or tapers, each surface 252, 254, and 256 is generally parallel to its respective corresponding surface 253, 255, 257. Furthermore, in one embodiment, the longitudinal distance or length $L_H$ of the head 250 between the left surface 256 and the right surface 257 is greater than the lateral distance or width $W_H$ between the left surface 254 and the right surface 255. Furthermore, the width $W_H$ is greater than the vertical distance or height $H_H$ between the lower surface 252 and the upper surface 253. Moreover, the length $L_H$ of the head 250 may be equal to the length $L_B$ of the base 210 and the width $W_H$ of the head 250 may be equal to the width $W_B$ of the base 210. However, other embodiments of the head 250 may possess a different distal relationship between the surfaces 252-257.

The shaft 230 generally extends vertically between and the base 210 and head 250 to affix the head 250 to the base 210. The shaft 230 may extend between central portions of the upper surface 212 of the base 210 and the lower surface 252 of the head 250. The shaft 230 may position the head 250 above the base 210 such that the lower surface 252 of the head 250 is positioned above and parallel to the upper surface 212 of the base 210. In this manner, the base 210 and head 250 may form a tapered left grip 260 and tapered right grip 280 opposite the tapered left grip 260. In particular, the tapered grips 260, 280 extend longitudinally from the shaft 230 such that each grip 260, 280 includes a proximal end 261, 281 adjacent to the shaft 230 and a grip inlet 271, 291 distal from the shaft 230. In particular, each grip inlet 271, 291 is associated with its respective end surfaces 216, 217, 256, 257, which are distal from the shaft 230. Each grip 260, 280 may laterally receive and secure a tether 50. Moreover, each grip 260, 280 may be implemented in a similar manner. As such, only the tapered grip 260 is described in detail below.

The tapered grip 260 may include the grip inlet 271 defined by a vertical gap between the left surface 216 of the base 210 and the left surface 256 of the head 250. The tapered grip 260 may further include one or more recesses 272 in the upper surface 212 of the base 210 and one or more recesses 274 in the lower surface 252 of the head 250. The recesses 272 may extend outward from the shaft 230 toward the left surface 216 of the base 210. Similarly, the recesses 274 may extend outward from the shaft 230 toward the left surface 256 of the head 250.

Figure 7:
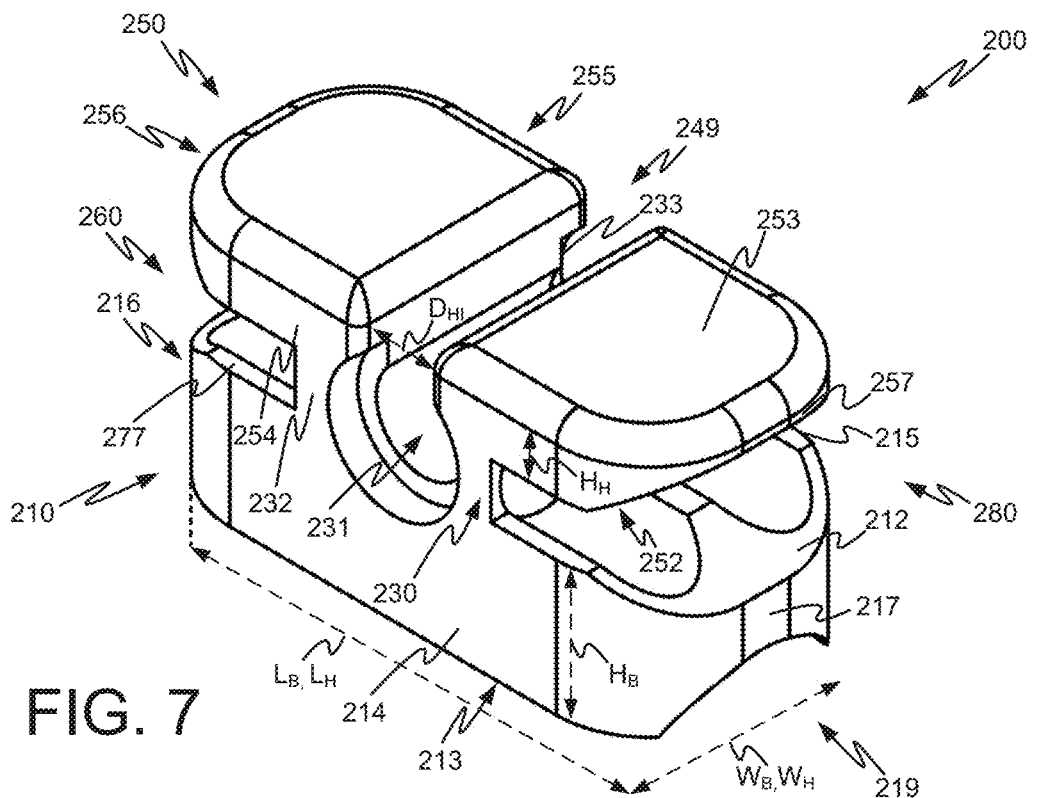
FIGS. 7-10 provide various views of one embodiment of a cleat affixed to a frame arm of the retractor system shown in FIG. 1.
Figure 8:
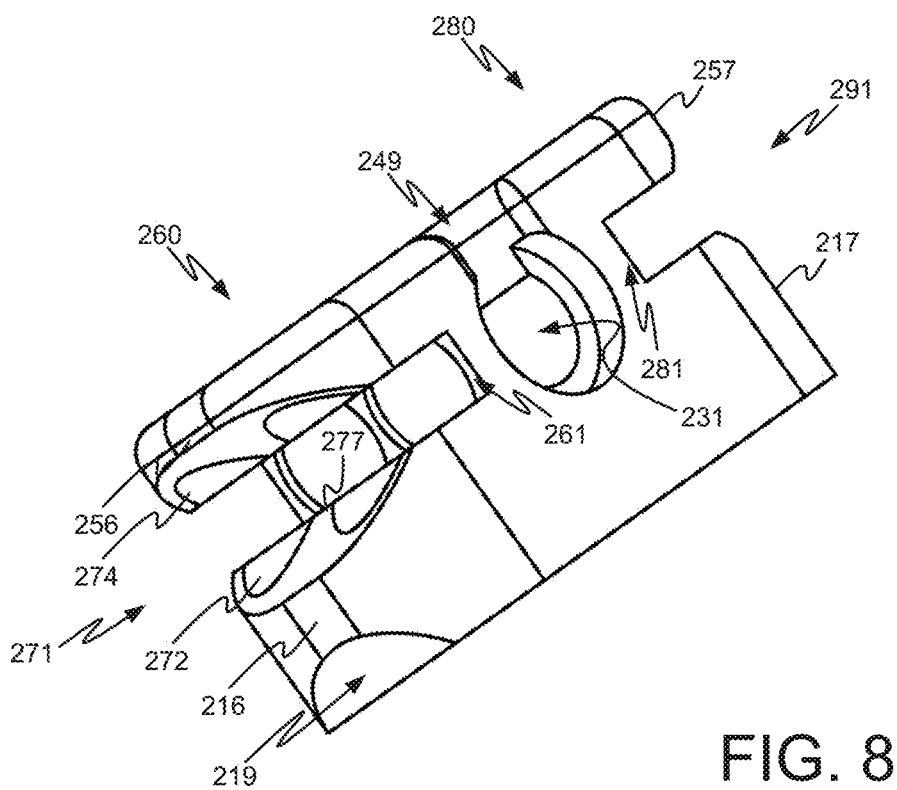
Figure 9:
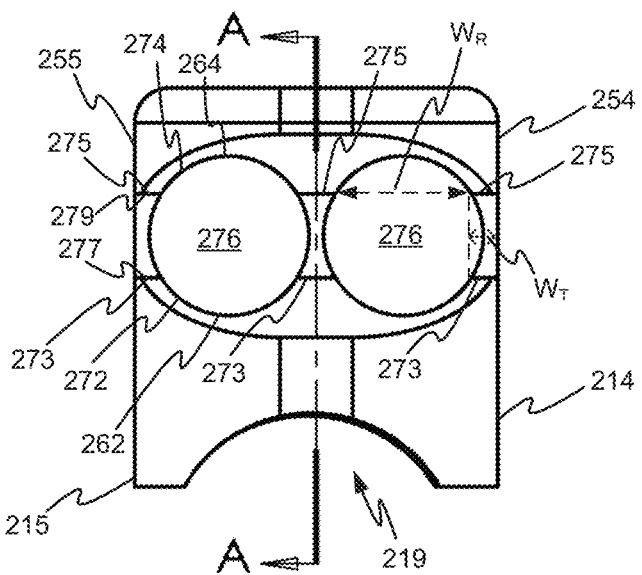

As shown in FIG. 9, a recess 272 in the base 210 may align with a corresponding recess 274 in the head 250 to define a generally cylindrical aperture 276 that extends between the shaft 230 and grip inlet 271. As further shown, the recesses 272 define a row of teeth 273 that project beyond respective depths 262 of the recesses 272. In particular, the row of teeth 273 spans across the upper surface 212 between a front side 214 and a back side 215 of the base 210, whereas each tooth 273 comprises a gripping surface 277 that extends outwardly from the shaft 230. Similarly, the recesses 274 define a row of teeth 275 that project beyond respective depths 264 of the recesses 274. The row of teeth 275 spans across the lower surface 252 between a front side 254 and a back side 255 of the head 250, whereas each tooth 275 comprises a gripping surface 279 that extends outwardly from the shaft 230. Furthermore, each tooth 273 of the base 210 has a corresponding, oppositely positioned tooth 275 of the head 250. However, in some embodiments, the teeth 273, 275 may not be directly opposite each other. Moreover, FIGS. 6-8 depicts three lower teeth 273 and three upper teeth 275. However, some embodiments may include more teeth 273, 275, and some embodiment may include fewer teeth 273, 275.

Figure 10:
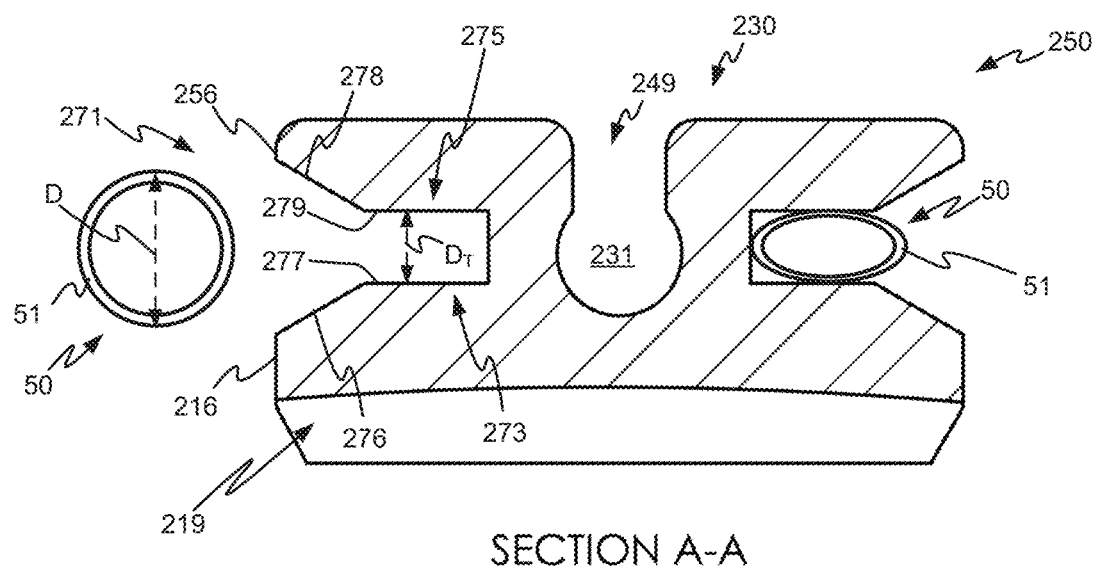

As shown in FIG. 10, the distance $D_T$ between opposite teeth 273, 275 is smaller than the distance $D_I$ between the upper surface 212 and the lower surface 252 of the grip inlet 271 due to taper surfaces 276, 278. In particular, taper surfaces 276 taper the upper surface 212 of the base 210 from left surfaces 216 to gripping surfaces 277 of the teeth 273. Similarly, taper surfaces 278 taper the lower surface 252 of the head 250 from the left surfaces 256 to gripping surfaces 279 of the teeth 275. In one embodiment, the distance between surfaces of the grip inlet 271 is greater than the diameter D of a tether 50 in order to laterally receive and guide lateral sides 51 of the tether 50 toward the gripping surfaces 277, 279. Moreover, the distance $D_T$ between gripping surfaces 277, 279 of opposite teeth 273, 275 is smaller than the diameter D of the tether 50, thus resulting in gripping surfaces 277, 279 radially compressing received lateral sides 51 of the tether 50 as shown in FIG. 10.

Furthermore, as depicted in FIG. 9, the width WT of the gripping surfaces 277, 279 may be smaller than the width $W_R$ of the recesses 272, 274. As such, the directly opposing teeth 273, 275 may radially compress lateral sides 51 of the tether 50 while considerable portions of the tether 50 remain uncompressed in the recesses 272, 274. Such uncompressed portions may help prevent the tether 50 from slipping along the row of teeth 273 or along the row of teeth 275.

In one embodiment, each gripping surface 277, 279 is generally a narrow, elongated surface that extends away from the shaft 230 toward the left surfaces 216, 256. As such, each gripping surface 277, 279 may engage elongated sides 51 of the tether 50 as the tether 50 spans across the row of teeth 273 and the row of teeth 275. In this manner, the gripping surfaces 277, 279 may radially pinch or compress elongated sides 51 of the tether 50 along multiple points and prevent the tether 50 from slipping along the row of teeth 273 or along the row of teeth 275.

In one embodiment, the gripping surfaces 277 of teeth 273 are parallel to the corresponding gripping surfaces 279 of directly opposite teeth 275. Such a parallel configurations of the gripping surfaces 277, 279 may retain the radially compressed tether 50 better than if the gripping surfaces 277, 279 were tapered toward the shaft 230 in a manner similar to tapered surfaces 276, 278. In yet another embodiment, the gripping surface 277, 279 are tapered toward the grip inlet 271 such that the separation between surfaces 277, 279 is greater closer to the shaft 230 than the separation between surfaces 277, 279 further from the shaft 230. Such tapered gripping surfaces 277, 279 may retain the compressed tether 50 better than parallel gripping surfaces 277, 279.

As further shown, the shaft 230 and the head 250 may be bifurcated. Such bifurcation may permit the cleat 200 to receive the tether 50 via a head inlet 249. In one embodiment, a cylindrical aperture 231 extends through the shaft 230 from a front surface 232 of the shaft to a back surface 233 of the shaft. Similarly, the head inlet 249 extends through the front surface 254 to the back surface 255 and extends through the upper surface 253 to the cylindrical aperture 231. Furthermore, a distance $D_{HI}$ between inner surfaces 248 of the head inlet 249 may be smaller than the diameter D of the tether 50. As such, the head inlet 249 may radially compress lateral sides 51 of the tether 50 as the tether 50 passes between the inner surfaces 248 and is received by the cylindrical aperture 231. In this manner, the head inlet 249 may help retain the tether 50 in the aperture 231.

Finally, as shown in FIGS. 7-9, the lower surface 213 of the base 210 may include a recess 219 that laterally spans the lower surface 213 from the left surface 216 to the right surface 217. In one embodiment, the recess 219 is sized to closely mate with the member 25 of the frame arm 24. In particular, a portion of the member 25 may have a general, cylindrical shape and the recess 219 may match the outer surface of such cylindrical shape.

Figure 11:
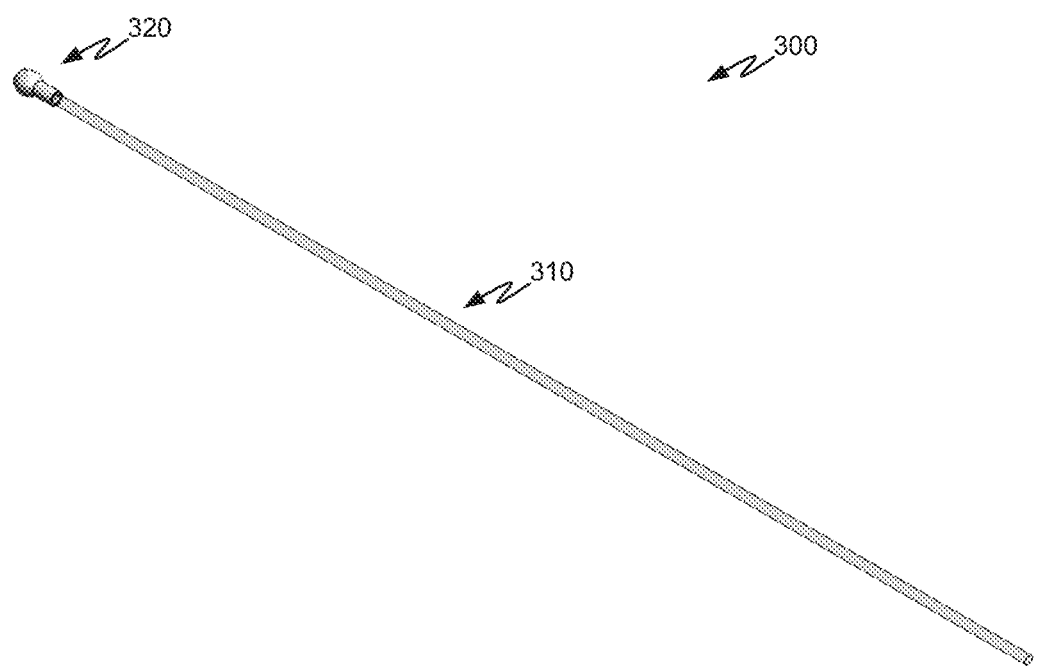
FIG. 11 provides a perspective view of one embodiment of a tether of the retractor system shown in FIG. 1.

Referring now to FIG. 11, an embodiment of a tether 300 is shown. In particular, the tether 300 may be used for the tether 50 mentioned above. As shown, the tether 300 may include an elongated, flexible, elastic member 310 having elongated sides 311. For example, the elastic member may comprise a latex rubber tubing having an a diameter of ⅛", ¼", or some other diameter. However, other elongated, elastic members may be suitable. Furthermore, the tether 300 may include a bulbous head 320 attached or integrated into one or both ends of the elastic member 320. In some embodiments, the head 320 comprising a metal such as surgical grade steel that is affixed to an end of the elastic member 310. In particular, the head 320 has a larger diameter than the diameter of the elastic member 310. Moreover, in embodiments in which the head 320 comprises metal, the head 320 may not compress under normal usage. As such, the head 320 may aid in securing the tether to one or more cleats 30 as the head 320 may be too large to pass through the grips 260, 280 and/or aperture 231.

In other embodiments, the head 320 is merely an enlargement of the elastic member 310. In such an embodiment, the head 320 may possess similar compression characteristics. However, due to its larger diameter, the head 320 may still prevent passage through the grip openings 270 and/or aperture 231 under normal usage. In yet further embodiments, the tether 300 may lack a head 320.

Figure 12:
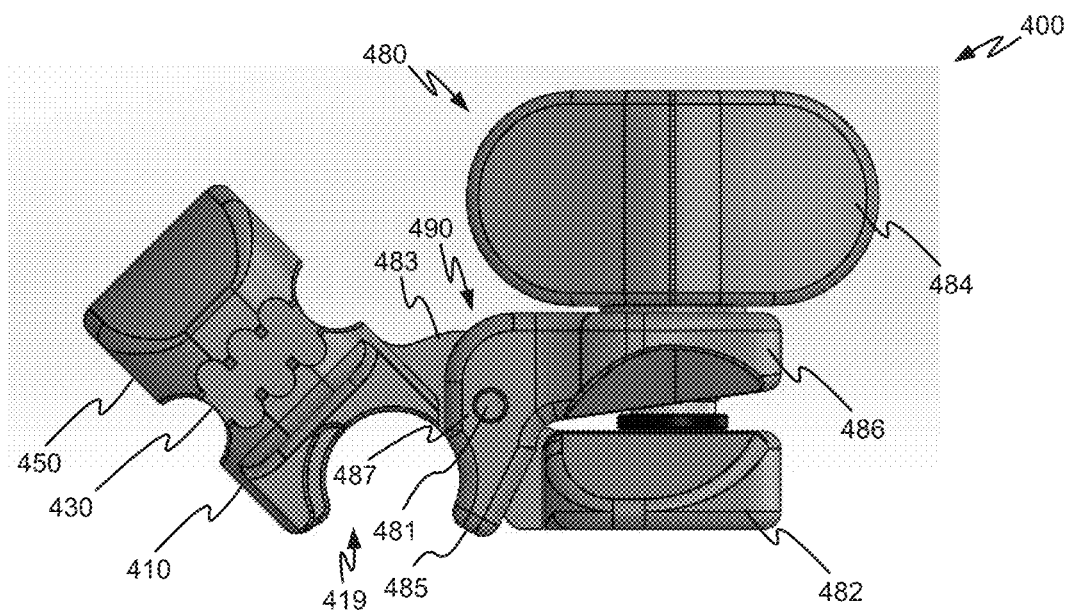
FIGS. 12-13 provide various views of another embodiment of a cleat that may be detachably coupled to a frame arm of the retractor system of FIG. 1.
Figure 13:
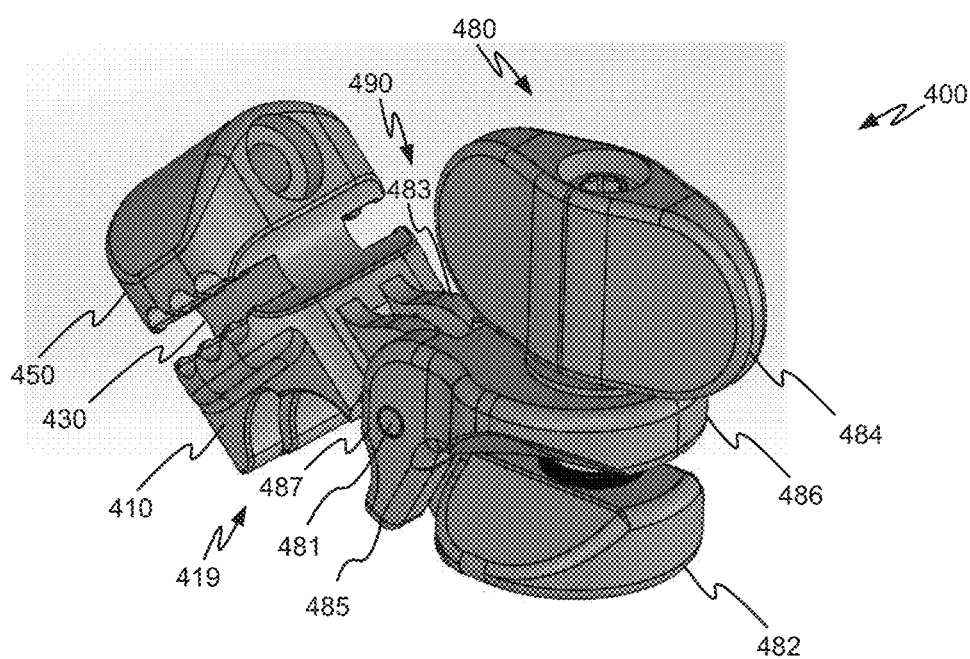

Referring now to FIGS. 12 and 13, an embodiment of a cleat 400 is shown. The cleat 400 is very similar to the cleat 200 described above as such the following focuses on the detachable coupling aspect of cleat 400. Whereas cleat 200 is permanently or semi-permanently affixed to the frame arms 24 via fasteners such as screws, rivets, etc., the cleat 400 is configured to be detachably coupled to frame arms 24. To this end, the cleat 400 includes a base 410, shaft 430, and head 450 that are similar to the base 210, shaft 230, and head 250 of cleat 200. However, the base 410 of the cleat 400 is further affixed to a lower member 482 of a clamp 480.

As shown, the clamp 480 includes a thumb screw 484 that passes through an upper member 486 and into the lower member 482. The lower member 482 includes one or more barrels 483 that interleave with one or more barrels 487 of the upper member 486. A pin 481 may pass through the barrels 483, 487 to form a hinge 490 that pivotably couples the upper member 486 to the lower member 482 and the affixed cleat 400.

Rotation of the thumb screw 484 causes the upper member 486 and lower member 482 and its affixed cleat 400 to pivot about pin 481. In particular, rotation of the thumb screw 484 in a first direction forces a projection 485 of the upper member 486 toward a recess 419 in the cleat 400. Conversely, rotation of the thumb screw 484 in a direction opposite the first direction forces the projection 485 away from the recess 419 in the cleat 400. In this manner, the projection 485 may be moved away from the recess 419 to permit the recess 419 to receive a frame arm 24. After receipt of the frame arm 24, the projection 485 may be forced toward the recess 419 in order to trap the frame arm 24 within the recess 419 and secure the cleat 400 to the frame arm 24.

Referring back to FIG. 1 general operation of the retractor system 10 will be described. To use the retractor system 10, the frame assembly 20 may be first secured to the hospital bed. With the patient in place, an incision may be made to provide access to the operative site of interest. A retractor 40 may be selected and inserted, distal end first, into the operative site of interest. The retractor 40 may be positioned as desired to retract tissue and provide access to the surgical site of interest. Once positioned as desired, the retractor 40 may be secured to the frame assembly 20 by wrapping a tether 50 about a handle 42 of the retractor 40 and one or more cleats 30 of the frame assembly 20. In this manner, the retractor 40 may be secured at both its distal and proximal ends, removing the need for manual holding of the retractor during the procedure.

Further, while the tether 50 maintains the retractor 40 in position, the tether 50 allows some amount of "float" of the retractor 40 relative to the frame assembly 20 in the event of any pounding, chiseling, or other events that may cause portions of the anatomy or equipment to shift, helping to maintain a desired access shape as well as helping to reduce risk of any additional injury or trauma to the patient, as well as damage to any equipment, that may be caused by such a shift or movement. Next, additional retractors 40 may be added, positioned, and secured in place as desired. Each of the retractors may be positioned independently of other retractors, in contrast to certain known systems that require, for example, paired blades to be located opposed to each other. Thus, the retractor system 10 provides for flexibility in the formation of the desired access site, as well as open access to the site of interest.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiments disclosed, but that the present disclosure includes all embodiments falling within the scope of the appended claims.

What is claimed is:

1. A cleat for securing a surgical retractor via an elastic tether having an elongated side and a predetermined diameter, the cleat comprising:
   a base comprising a base upper surface, a base lower surface, and first teeth along the base upper surface;
   a head comprising a head upper surface, a head lower surface, and second teeth along the head lower surface; and
   a shaft comprising at least one shaft sidewall that:
      extends upward from the base upper surface to the head lower surface; and
      separates the base upper surface from the head lower surface by a gap based on a length of the at least one shaft sidewall between the base upper surface and the head lower surface;
   wherein each tooth of the first teeth is separated from a respective opposing tooth of the second teeth by less than the predetermined diameter of the tether; and
   wherein each tooth of the first teeth and its respective opposing tooth of the second teeth compress the elongated side of the tether when received therebetween;
   wherein the shaft couples a central portion of the base to a central portion of the head;
   wherein the at least one shaft sidewall comprises a shaft first sidewall and a shaft second sidewall opposite the shaft first sidewall;
   wherein the shaft first sidewall and the shaft second sidewall traverses the gap between the base upper surface and the head lower surface;

wherein a first base portion and a first head portion protrude from the shaft first sidewall in a first direction;

wherein a second base portion and a second head portion protrude from the shaft second sidewall in a second direction;

wherein a distal end of the first base portion and a distal end of the first head portion define a first grip inlet to the first teeth and the second teeth; and wherein a distal end of the second base portion and a distal end of the second head portion define a second grip inlet.

2. The cleat of claim 1, wherein:

an upper surface of the second base portion includes third teeth;

a lower surface of the second head portion includes fourth teeth; and wherein each tooth of the third teeth is separated from a respective opposing tooth of the fourth teeth by less than the predetermined diameter of the tether; and wherein each tooth of the third teeth and its respective opposing tooth of the fourth teeth compress the elongated side of the tether when received therebetween.

3. The cleat of claim 1, wherein the distal end of the first base portion and the distal end of the first head portion taper the first grip inlet toward gripping surfaces of the first teeth and the second teeth.

4. A cleat for securing a surgical retractor via an elastic tether having an elongated side and a predetermined diameter, the cleat comprising:

a base comprising a base upper surface, a base lower surface, and first teeth along the base upper surface;

a head comprising a head upper surface, a head lower surface, and second teeth along the head lower surface; and a shaft comprising at least one shaft sidewall that:
extends upward from the base upper surface to the head lower surface; and
separates the base upper surface from the head lower surface by a gap based on a length of the at least one shaft sidewall between the base upper surface and the head lower surface;

wherein each tooth of the first teeth is separated from a respective opposing tooth of the second teeth by less than the predetermined diameter of the tether; and wherein each tooth of the first teeth and its respective opposing tooth of the second teeth compress the elongated side of the tether when received therebetween;

wherein the shaft comprises an aperture extending through the shaft from a shaft front surface to a shaft back surface;

wherein the head upper surface comprises an inlet configured to receive the elongated side of the tether; and wherein the inlet in the head upper surface provides a passage through the head upper surface to the aperture.

5. The cleat of claim 4, wherein each tooth of the first teeth comprises:

a root coupled to the base upper surface; and a tip distal from the root, wherein the tip provides an elongated, gripping surface that extends from a first portion of the tip that is proximal to the shaft to a second portion of the tip that is distal from the shaft.

6. The cleat of claim 5, wherein each tooth of the second teeth comprises an elongated, gripping surface that is parallel to the elongated, gripping surface of an opposing tooth of the first teeth.

7. The cleat of claim 6, wherein:

the first teeth are defined by one or more first recesses in the base upper surface; and the second teeth are defined by one or more second recesses in the head lower surface.

8. The cleat of claim 7, wherein:

a lateral width of each elongated, first gripping surface is smaller than a lateral width of each first recess; and a lateral width of each elongated, second gripping surface is smaller than a lateral width of each second recess.

9. The cleat of claim 4, wherein the base lower surface comprises a recess that extends between a first base end that is distal from the shaft and a second base end that is distal from the shaft.

10. The cleat of claim 9, further comprising:

a clamp comprising an upper member pivotably coupled to a lower member; wherein the base is coupled to the lower member of the clamp; and wherein the upper member comprises a projection configured to capture a frame member in the recess in the base lower surface when the upper member is pivoted toward a closed position with respect to the lower member.

11. The cleat of claim 4, wherein each tooth of the base upper surface is separated from a respective opposing tooth of the head lower surface by a same distance that is less than the predetermined diameter of the tether.

12. A cleat for securing a surgical retractor via an elastic tether having an elongated side and a predetermined diameter, the cleat comprising:

a base comprising an upper surface with a first row of teeth;

a head coupled to the base via a shaft, the head comprising a lower surface with a second row of teeth;

wherein the first row of teeth are opposite the second row of teeth by less than the predetermined diameter of the tether and are configured to receive and compress the elongated side of the tether;

wherein the base comprises a lower surface opposite the upper surface of the base; and wherein the lower surface comprises a recess that extends between a first surface of the base that is distal from the shaft to a second surface of the base that is distal from the shaft.

13. The cleat of claim 12, further comprising:

a clamp comprising an upper member pivotably coupled to a lower member; wherein the base is coupled to the lower member of the clamp; and wherein the upper member comprises a projection configured to capture a frame member in the recess in the lower surface of the base when the upper member is pivoted toward a closed position with respect to the lower member.

14. A retractor system, comprising:

an elastic tether having an elongated side and a predetermined diameter; and a frame arm comprising a cleat;

wherein the cleat comprises:

a base comprising a base upper surface, a base lower surface affixed to the frame arm, and first teeth along the base upper surface;

a head comprising a head upper surface, a head lower surface, and second teeth along the head lower surface; and a shaft comprising at least one shaft sidewall that separates the base upper surface from the head lower surface by a gap traversed by the at least one shaft sidewall;

wherein each tooth of the first teeth is separated from a respective opposing tooth of the teeth by less than the predetermined diameter of the tether; and wherein each tooth of the first teeth and its respective opposing tooth of the second teeth compress the elongated side of the tether when received therebetween.

15. The retractor system of claim 14, further comprising:

a surgical retractor comprising a retractor blade coupled to a handle;

wherein the elastic tether is wrapped around the handle of the surgical retractor; and wherein the surgical retractor is secured to the cleat via the elastic tether and radial compression of the elongated side of the elastic tether by the first teeth and the second teeth.

16. The retractor system of claim 14, wherein:

the base lower surface of the cleat comprises a recess that extends between a first base end that is distal from the shaft and a second base end that is distal from the shaft; and the cleat is affixed to the frame arm such that a portion of the frame arm is received by the recess and extends along the recess from the first base end to the second base end.

17. The retractor system of claim 14, further comprising a clamp that affixes the cleat to the frame arm.

18. The retractor system of claim 14, wherein the frame arm comprises a plurality of the cleat.

19. The retractor system of claim 14, wherein:

each tooth of the first teeth comprises a root coupled to the base upper surface, and a tip distal from the root, wherein the tip provides a gripping surface that extends from a first portion of the tip that is proximal the shaft to a second portion of the tip that is distal from the shaft; and each tooth of the second teeth comprises a tip that provides a gripping surface that is parallel to the gripping surface of an opposing tooth of the first teeth.

* * * * *